United States Patent [19]

Eichelburg

[11] 4,265,913

[45] * May 5, 1981

[54] ORAL INGESTA FOR ANIMALS

[76] Inventor: Robert J. Eichelburg, Woodland Rd., Pound Ridge, N.Y. 10576

[*] Notice: The portion of the term of this patent subsequent to Dec. 28, 1993, has been disclaimed.

[21] Appl. No.: 653,214

[22] Filed: Jan. 28, 1976

Related U.S. Application Data

[63] Continuation of Ser. No. 448,208, Mar. 5, 1974, Pat. No. 3,997,675, and Ser. No. 463,314, Apr. 23, 1974, Pat. No. 4,000,319, and a continuation of Ser. No. 473,347, May 28, 1974, abandoned.

[51] Int. Cl.$^3$ ................................................. A23K 1/00
[52] U.S. Cl. .......................................... 426/2; 426/62; 426/650; 426/805; 424/93
[58] Field of Search .................... 426/2, 62, 289, 293, 426/295, 534, 650, 533, 635, 656, 805; 424/93

[56] References Cited

U.S. PATENT DOCUMENTS

| | | | |
|---|---|---|---|
| 2,764,487 | 9/1956 | Wilkerham | 426/60 |
| 2,946,688 | 7/1960 | Rosenthal | 426/60 |
| 3,739,976 | 1/1973 | Bunting | 426/60 |
| 3,740,423 | 6/1973 | Barbier | 424/93 |
| 3,830,798 | 8/1974 | Herndon | 426/175 |
| 3,946,114 | 3/1976 | Tsao | 426/656 |
| 4,000,319 | 12/1976 | Eichelburg | 426/805 |

FOREIGN PATENT DOCUMENTS 2096887  3/1972  France ........................................ 424/93

OTHER PUBLICATIONS

The Yeasts-Lodder North-Holland Pub. Co., Amsterdam 1970, pp. 894-898, 1064.
Chem. Abs. V 71, 1969, 42326g.

Primary Examiner—Hiram Bernstein

[57] ABSTRACT

The palatability of oral ingesta, such as animal food or orally administered animal medicaments is improved by combining such ingesta with yeast from the genera ascomycetous yeasts or asporogenous yeasts. Oral ingesta such as an animal medicament or animal food is combined with either *Torulopsis utilis* or *Saccharomyces cerevisiae*.

10 Claims, No Drawings

ORAL INGESTA FOR ANIMALS

BRIEF SUMMARY OF THE INVENTION

The present invention is a Continuation in Part of my co-pending United States patent applications Ser. No. 448,208 filed Mar. 5, 1974 now U.S. Pat. No. 3,997,675 and Ser. No. 463,314 filed Apr. 23, 1974 now U.S. Pat. No. 4,000,319, and a Continuation of my co-pending U.S. application Ser. No. 473,347, filed May 28, 1974 now abandoned.

The palatability of oral ingesta such as an animal food or orally administered animal medicaments is improved by combining such food with yeast from the genera ascomycetous yeast or asporogenous yeast. The yeast-like genera belonging to the order Ustilaginales (in the Basidiomvcetes) and the yeast-like genera belong to the family Sporobolomycetaceae are also within the broad scope of the invention. In one embodiment, the palatability of oral ingesta such as animal food or animal medicaments such as dog or cat food or orally administered medicaments for cats or dogs is improved by coating such food with yeasts comprising either Torulopsis, Candida, or Saccharomyces. An outstanding feature of the invention is that the yeasts suitable for improving the palatability of such ingesta are high in essential B vitamins and proteins. The ingesta combined with yeasts according to the invention may also be used in the dry state, the palatability not being dependent on the addition to or incorporation of water or liquid to improve flavor or release flavor ingredients. Water or other liquids however may be employed, if desired. The examples describe the results obtained by combining an animal medicament and a comestible suitable for use as animal food with *Torulopsis utilis* and *Saccharomvces cerevisiae.*

DETAILED DESCRIPTION OF THE INVENTION

The present invention relates to oral ingesta such as animal food or orally administered animal medicaments especially such animal food or medicament of improved palatability. More specifically, the present invention relates to animal food or orally administered animal medicaments such as dog food or medicaments and cat food or medicaments having improved palatability.

Problems have been encountered with the prior art canned, dry and moist animal food in that some canned pet food although having good palatability, was low in nutritional value because anywhere from 60–70% of the canned food comprised water and further the ingredients of such canned foods were qualitatively lacking in the nutritive food values essential for sustaining animal health.

On the other hand, commercially-available dry animal food generally has low to poor palatability but is exceptionally high in nutritive value. This dry animal food is supplied as kibs which are spheres, cylinders or cubes of anywhere from about $\frac{1}{8}$" to about $\frac{1}{4}$" maximum dimension. The lack of palatability or poor palatability affects animal nutrition in that the animal fed with such food would not consume enough of the food to maintain proper health. Consequently several attempts have been made in the prior art to improve the palatability of dry animal food kibs as set forth in U.S. Pat. No. 3,119,691 Ludington et al. in which the kib has applied to it a coating which forms a gravy containing mixture upon addition of water.

One of the difficulties with the prior art dry animal food kibs having a coating which forms a gravy containing mixture on the addition of water was that after the kib had been treated with water the kib would tend to soften after standing about 12 hours, the animal would no longer be interested in the food and, consequently, the food had to be thrown out. Additionally, if the kibs were wet and allowed to stand for a sufficient length of time, the likelihood of spoilage would increase thereby negating the long storage properties of the dry kibs. This would be a particular disadvantage if the animal had to be left food for one or more days. Furthermore, the user of the food had to go to the difficulty of mixing up the dry animal food kibs with water prior to use which involved an extra step in the preparation of the animal food which detracts from the ready-to-use characteristics of dry food.

The prior art also teaches improvement in the palatability of dry animal food kibs by the addition of liquid beef extract such as beef broth or fish scrap. It has been observed, however, that even with the addition of liquid beef extracts, such as beef broth or fish scrap, to standard commercially-prepared dry animal food kibs, the resultant dry animal food kib does not have sufficient palatability to induce an animal to eat sufficient amounts of the animal food to maintain proper nutrition.

One of the other problems encountered in the prior art was the difficulty in formulating substantially farinaceous animal food such as those based on grains that include rye, wheat, oats, barley and corn to be palatable to carnivores. Admixing farinaceous materials with meat, meat by-products, and meat meal as additives and extracts thereof as flavorants were generally the method employed in the prior art to improve the palatability of farinaceous materials however this was generally expensive and of limited success. Similar problems were encountered in the prior art with formulating vegetable protein animal food to be palatable for carnivores. Again vegetable proteins admixed with meat, meat by-products, meat meal and extracts thereof was a method for obviating the problems as employed in U.S. Pat. No. 3,202,514 Burgess et al. with the attendant aforementioned drawbacks of high cost and limited success in avoiding the problem.

It has also been observed that moist animal food as described in U.S. Pat. No. 3,202,514 Burgess et al. although having improved palatability over commercially-available dry animal food, the palatability of this moist animal food is not at an optimum and decreases after a period of about two days after unpackaging.

An additional problem with the prior art flavorants for animal food is that they are extremely low in any nutritive value.

The administration of oral medicaments to animals such as cats or dogs is also difficult because most medicaments have a taste offensive to the animal. This may be partially obviated by mixing the medicament with the animal food; however, if the animal is suffering from a loss of appetite or diminished appetite as one symptom of a disease or disorder, the food will not be fully consumed and consequently less than the recommended dosage will be taken. In some instances, this can be obviated by resorting to injectable medicaments as in the case of penicillin which may be administered orally as in the case of Pen-V and Ampicillin or may be injected such as Pen G or semi-synthetic penicillin such as Carbenicillin. Injectables present some difficulty in use in that trained personnel are required for their administration, some discomfort is suffered by the animal and administration requires special equipment, i.e., a hypodermic needle and syringe. Additionally, not all medicaments are available as injectables or in oral dosage units as are the penicillin. It would therefore be desirable to improve the palatability of orally administered animal medicaments to assure full dosage is received by the animal and to avoid the other aforementioned difficulties associated with the non-oral administration of such medicaments.

It is therefore an object of the present invention to overcome these and other difficulties of the prior art and especially to provide a process for improving the palatability of oral ingesta such as animal food and orally administered medicaments for animals as well as to provide an article of manufacture comprising ingesta such as animal food and orally administered medicaments for animals having improved palatability.

It is a further object of the present invention to provide a process for improving the palatability of such ingesta and to provide an article of manufacture comprising such ingesta having improved palatability which does not require the addition of water or any other liquid to obtain such improved palatability.

It is a further object of the present invention to provide as an article of manufacture ingesta such as animal food which are substantially farinaceous compositions or vegetable protein compositions or mixtures thereof that are palatable to carnivores. It is also an object of the invention to provide a method of making a substantially farinaceous comestible or vegetable protein ingesta or mixtures thereof palatable to a carnivore without the use of meat, meat by-products, meat meal or extracts thereof.

It is a further object of this invention to improve the palatability of ingesta such as moist animal food of from about 15 to about 30% by weight moisture; meat or meat by-products or meat meal or mixtures thereof; vegetable protein and optionally from about 15% to about 30% by weight of sugar.

It is also an object of the present invention to provide a process for improving the palatability of such ingesta and to provide an article of manufacture comprising such ingesta having improved palatability by means of a product that is high in B vitamins and amino acids.

These and other objects have been achieved by the present invention in which an article of manufacture is provided comprising ingesta such as animal food and orally administered medicaments for animals which has been combined with yeast. Throughout the specification, the ingesta of the present invention is described as being combined with yeast by which it is meant that such yeast may be employed as a surface coating on such ingesta or in admixture with such ingesta or both. Yeasts from either the group ascomycetous or asporogenous have been found to be effective in this regard. The yeast-like genera belonging to the order Ustilaginales (in the Basidiomycetes) and the yeast-like genera belong to the family Sporobolomycetes) and the yeast-like genera belong to the family Sporobolomycetaceae are also within the broad scope of the invention. The yeasts employed in accord with the present invention are further identified in the publication. The Yeasts, *A Taxonomic Study*, edited by J. Lodder, 1970.

The various genera of yeasts within the group ascomycetous which can be employed according to the present invention include Endomycopsis, Kluyveromyces, Saccharomyces, Saccharomycodes, Saccharomycopsis, and Schizosaccharomyces.

The various genera of asporogenous yeasts that can be employed according to the present invention especially asporogenous yeast not belonging to the Sporobolomycetaceae include Candida, Oosporidium and Torulopsis.

The species of yeast in the group asporogenous that can be employed to advantage according to the present invention comprise *Torulopsis utilis* (*Candida utilis*) and *Candida arborea*, *Oospora lactis* (*Oidium lactis*, *Endomyces lactis*, *Geotrichum candidum*).

Because of the commercial usage the term "Torula yeast" or "torula yeast" is employed to designate the species *Torula utilis*, *Torulopsis utilis* and *Candida utilis*, the latter three being treated as synonyms in *The Yeasts, supra*. The genera Candida and Torulopsis are maintained as separate genera in *The Yeasts, supra* for the reasons stated at pages 894–897 thereof because a reclassification into natural taxa is considered "inadvisable since it would make necessary the provisory renaming of a great number of species. This would inevitably lead to confusion and justified irritation among the increasing number of workers in various fields who use or encounter yeast of this group."

The various species within the group ascomycetous which are also employed to advantage according to the present invention comprise *Saccharomyces cerevisiae*, *Saccharomyces cerevisiae* variety *ellipsoidus*, *Saccharomyces carlsbergensis* and *Saccharomyces fragilis* (*Kluyveromyces fragilis*).

The genera of yeasts preferred in accord with the present invention comprise Torulopsis, Candida and Saccharomyces.

Commercially-available dried yeast which are used according to the present invention includes either primary dried yeast or secondary yeasts which may be classified as follows:

1. Primary dried yeast—*Saccharomyces cerevisiae*
2. Primary dried torula yeast—*Torulopsis utilis* (*Candida utilis*)
3. Secondary yeast, brewer's dried yeast—*Saccharomyces cerevisiae*, *Saccharomyces carlsbergensis*

The composition of commercially-available dried primary yeast is given in the 11th Edition of *The National Formulary*, pages 395–396 and is as follows:

| protein (N × 6.25) | minimum | 45% |
| thiamine hydrochloride (vitamin $B_1$) | minimum | 120 µg/g |
| riboflavin (vitamin $B_2$) | minimum | 40 µg/g |
| nicotinic acid | minimum | 300 µg/g |
| fermenting power | inactive | |
| fillers | none | |
| total bacterial count | maximum | 7500 µg/g |
| mold count | maximum | 50 µg/g |
| moisture | maximum | 7% |
| ash | maximum | 8% |

Primary dried yeasts which are marketed for food usage have the following analysis which is considered typical:

| moisture | 5.0% | calcium | 0.3% |
| protein | 50.0% | phosphorous | 2.4% |
| fat (ether ext.) | 1.2% | potassium | 2.6% |

| | | | |
|---|---|---|---|
| total lipids | 5.5% | magnesium | 0.5% |
| carbohydrates | 31.5% | sodium | 0.4% |
| ash | 8.0% | | |

The amino acid content of primary dried yeast is approximately as follows as expressed as a percent of dried proteins:

| | | | |
|---|---|---|---|
| alanine | 9.0% | lysine | 8.2% |
| arginine | 5.0% | methionine | 2.5% |
| aspartic acid | 4.0% | phenylalinine | 4.5% |
| cystine | 1.6% | proline | 2.5% |
| glutamic acid | 13.5% | threonine | 5.5% |
| glycine | 0.6% | (and serine) | |
| histidine | 4.0% | tryptophan | 1.2% |
| hydroxyproline | 4.5% | tyrosine | 5.0% |
| isoleucine | 5.5% | valine | 5.5% |
| leucine | 8.0% | others | 9.4% |

All essential amino acids are present as can be seen from the above analysis. The vitamin contents of the various products are as follows in $\mu g/g$:

| | |
|---|---|
| thiamine | up to 10,000.0 |
| riboflavin | up to 12,000.0 |
| niacin | up to 30,000.0 |
| pyridoxine | 15.0 |
| pantothenic acid | 110.0 |
| biotin | 2.5 |
| inositol | 4,000.0 |
| choline | 4,000.0 |
| p-aminobenzoic acid | 13.0 |
| folic acid | 11.0 |

Secondary yeasts are those yeasts which are obtained upon the completion of brewery operation or production of alcohol from molasses and rum production, and is then subject to a purification after which it is dried to about 90% solids content and marketed as dried distiller's or dried brewer's yeast.

Primary and secondary brewer's dried yeast have approximately the same analyses.

Secondary brewer's dried yeast analysis typically as follows:

| | | | |
|---|---|---|---|
| protein | 50.0% | zinc | 38.7 ppm |
| fat | 1.5% | salmonella | negative |
| fiber | 1.5% | coliform | |
| ash | 7.0% | bacteria | negative |
| moisture | 6.0% | thiamine | 56.6 mg/lb |
| nitrogen-free | | riboflavin | 16.0 mg/lb |
| extract | 34.0% | niacin | 225.5 mg/lb |
| calcium | 0.12% | pantothenic | |
| phosphorous | 1.50% | acid | 55.2 mg/lb |
| potassium | 0.86% | pyridoxine | 22.6 mg/lb |
| iron | 0.02% | choline | 2200.0 mg/lb |
| copper | 35 ppm | betaine | 544.0 mg/lb |
| manganese | 5.3 ppm | biotin | 0.5 mg/lb |
| cobalt | 1.5 ppm | folic acid | 22.2 mg/lb |
| | | inositol | 2265.0 mg/lb |

Other yeast which are suitable for the purposes of the present invention comprise vitamin enriched yeasts which are manufactured by the addition of vitamins such as vitamins B1, B2 and B6 to the broth in which the yeast is grown and from which the yeast will subsequently absorb the vitamins. One of the outstanding features of the yeast used in accord with the present invention is they synthesize vitamin B1 in large quantities during production by coupling thiazole and pyrimidine when these compounds are added to the medium in which the yeast is grown. Yeast which are made by the addition of thiazole and pyrimidine and vitamin-enriched yeasts manufactured according to U.S. Pat. No. 2,262,635 Schultz, et al., U.S. Pat. No. 2,359,521 Harrison and U.S. Pat. No. 2,328,025 Mead et al. are also included within the scope of the present invention. Hydrolyzates of the foregoing yeasts may also be used according to the present invention and are prepared either by hydrolyzing such yeasts in a dilute aqueous hydrochloric acid solution or by an aqueous bacterial hydrolysis both of which are known in the art. The hydrolyzate thus obtained is dried and concentrated and employed in the same manner as the yeasts described herein. Any mixture of yeasts and/or hydrolyzates may also be employed according to the invention.

The farinaceous ingesta of the present invention may be made from any of the more common grains, such as corn meal, red dog flour, wheat germ, rye flour, wheat flour, oats, barley, and the like, and any combination thereof.

The farinaceous ingesta utilizing the foregoing common grains or farinaceous materials may be prepared by methods well known in the baking art. The grains are ground into a flour-like consistency to which is added a liquid a shortening and, optionally, a leavening agent, such as baker's yeast or baking powder, and the mixture then baked at a suitable temperature for a fixed period of time. In one embodiment of the present invention, the farinaceous ingesta prepared with a leavening agent is shaped into a crouton-like configuration having dimensions of approximately ¼" square dried at 110° F. for two hours and subsequently coated with the yeast of the present invention.

The ingesta of the present invention may also be made from vegetable protein materials which comprises oil seeds and legumes as well as the oil expressed or extracted meals and cakes and protein isolates thereof recovered by acid or alkali digestion and precipitation. Vegetable protein materials in this respect comprise soy beans, soy bean meal, soy bean powder, cotton seed meal, peanuts, peanut meal and the like and mixtures thereof.

The vegetable protein material may be used by itself. By way of example soy powder is pelletized by compression in a press into a ¼" diameter by ⅛" thickness round pellet and these pellets in turn are coated with the aforementioned yeast or 30% by weight of such yeast is admixed with the soy powder prior to pelletizing.

Mixtures of the farinaceous materials and protein materials, especially vegetable protein materials may be effected for example by substituting approximately 10% by weight of the grain flour previously described with soy powder and/or 10% by weight of yeast and the baked goods prepared with this substitution. This combination of farinaceous material with the vegetable protein material may also be coated with the yeast previously described.

The moist animal food which is also combined with the yeast in accord with the present invention is described in U.S. Pat. No. 3,202,514 Burgess et al. such moist animal food generally comprising from about 15 to about 30% by weight of moisture; from about 15 to about 30% by weight of sugar, meat or meat by-products or meat meal or mixtures thereof as meat protein material; and vegetable protein material as described previously, all of these terms being further described in U.S. Pat. No. 3,202,514 Burgess et al. along with other components employed in such moist animal food and the method for its manufacture.

The ingesta of the invention comprising animal food are thus prepared from farinaceous materials, or proteinaceous materials or mixtures of farinaceous and proteinaceous materials. Where the ingesta comprises mixtures of farinaceous and proteinaceous materials, anywhere from about 2% to about 98% by weight of farinaceous material, especially from about 5% to about 80% by weight of farinaceous material is employed, the balance comprising proteinaceous material.

The proteinaceous material, whether employed by itself or in combination with the farinaceous material may be vegetable protein or meat protein or mixtures of both vegetable protein and meat protein. Where mixtures comprising vegetable protein and meat protein are employed, the vegetable protein comprises anywhere from about 2% to about 95% by weight of the mixture and especially from about 5% to about 85% by weight of the mixture the balance comprising meat protein.

Since other ingredients may be used in the manufacture of the ingesta or are present therein such as water the farinaceous and/or proteinaceous materials will constitute anywhere from about 95% to about 5% by weight, especially from about 95% to about 60% by weight of the ingesta.

The ingesta of the invention may be dry by which it is meant it may contain anywhere from about 5% to about 12% by weight of water based on the ingesta; or it may be moist by which it is meant it may contain anywhere from above about 12% to about 40% by weight of water based on the ingesta; or wet at >40% water.

The oral medicaments which may be used in combination with the yeast according to the invention comprise those compositions and/or compounds in the *Physician's Desk Reference*, 29th Ed. (1974). The oral medicaments comprise inter alia compounds and/or compositions generally known as amebicides and trichomonacides, analgesics, anorexics, antiarthritics, antibacterials and antibiotics, anticoagulants, anticonvulsants, antidepressants, antihistamines, antineoplastics, anti-Parkinsonism drugs, antipyretics, antispasmodics and anticholinergics, antiviral agents, ataractics, cardiovascular preparations, contraceptives, diuretics, fertility agent, hematinics, hormones, laxatives, parasympathetic agents and parasympathomimetics, psychostimulants, sedatives, sympathomimetics and combinations and thyroid preparations. Compounds and/or compositions within the aforementioned classes include inter alia the following generic materials; methamphetamine, methcyclothiazide, cephalexmin, cephaloglycin, cloxacillin, phenoxyethyl penicillin, erythromycin, pargyline, ephedrine, codeine, methycyclothiazide, metharbital, deserpidine, pentobarbital, isoproterenol, piperazine, estrone, hydrochlorothiazide, ethchlorvynol, chlorazepate, sulfamethizole, phenazopyridine, oxytetracycline, pentaerythritol tetranitrate, diethylstilbestrol, 1-hyoscyamine, ethaverine, pentylenetetrazol, griseofulvin, ampicillin, phendimetrazine, meprobamate, conjugated estrogens, testosterone, pralidoxime, dicloxacillin, isoniazid, methanamine mandelate, phenacetin, aspirin, caffeine, hydrocodone bitartrate, oxacillin, phentermine, bisacodyl NF, phenmetrazine, ephedrine, glyceryl guaiacolate, phenobarbital, theophylline, sulfonamide, phenoxymethyl penicillin, kanamycin, tetracycline, hetacillin, metampicillin, aluminum glycinate, acetaminophen, salicylamide, methyltestosterone, bephenium hydroxynaphthoate, erythrityl tetranitrate, procyclidine, digoxin, cyclizine trimethoprim, sulfamethoxazole, benzyl penicillin, papaverine, hydralazine, allobarbital, acetaminophen, methandrostenolone, dimethindene, xylometazoline, tolazoline, tripenalennamine, reserpine, adiphenine, ethinamate, belladonna, piperacetazine, rifampin, warfarin, promethazine, sulfinpyrazone, phenylbutazone, oxyphenbutazone, carbamazepine, imipramine, furosemide, glycerol trinitrate, isoproterenol, bromisovalum, pentylenetetrazol, isometheptene, oxyphenonium bromide, amantadine, lithium carbonate, butyrophenone, hydroxyzines, chorionic gonadotropin, menotropins, cyanocobalamin, dipyridamole, casanthranol, dioctyl sodium sulfosuccinate, methylphenidate, thyroxine, amphetamine, chlordiazepoxide, diazepam and sulfisoxazole.

The ingesta article of manufacture may be in the shape of a kib which is a sphere, cylinder or cube or other three dimensional shape having a maximum dimension of from about ⅛" to about ¾". The article of manufacture may also be biscuit shaped, wafer shaped or any shape commonly used for animal food or orally-administered animal medicaments. Biscuits may be anywhere from about ½" to 2" in diameter and have a thickness of about 5% to about 50% of the diameter. Wafers may be anywhere from about ½" to about 6" in length, about ½" to about 3" in width and have a thickness anywhere from about 5% to about 50% of the width. The wafers may also be bone shaped. The ingesta may also be prepared as a continuous cylindrical, triangular, rectangular etc. extrudate of about ¼" in diameter.

The yeast when combined with the ingesta as a coating may be applied to all sides or only one side or any combination of sides of the ingesta. The coating may also be applied as stripes on the side of the ingesta or what will be defined herein as flavor channels which are grooves having a depth of from about 1% to about 20% of the maximum thickness of the ingesta and are filled with the yeast coating. A continuous coating of yeast or flavor channels may be applied by continuous coextrusion of the ingesta and yeast through an extrusion die.

The ingesta such as animal food or orally-administered animal medicaments are combined with greater than about 2% by weight or anywhere from about 2% to about 99% by weight of yeast either as a coating on the surface or in the flavor channels or in admixture with such ingesta where the aforesaid weight percent of yeast is based on dry yeast, i.e., yeast having from about 3 to about 10% by weight of water. In a further embodiment the ingesta of the invention have greater than about 5% and especially greater than about 7% or from about 5% to about 99% especially from about 7% to about 99% by weight of such yeast combined therewith as an admixture or coating.

Where the ingesta of the invention comprises orally-administered medicaments, in addition to the foregoing ranges the yeast may also be combined with such medicament in an even lesser amount such as, for example, in an amount greater than about 0.5%, such as anywhere from about 0.5% to about 99% by weight, the lower concentrations being especially effective when applied as a coating on such medicament.

The prior art discloses that yeast may be employed in animal food in concentrations up to about 0.5% as a B vitamin supplement; however, when yeast is used in admixture with animal food in such low concentrations it has no effect on improving the palatability of the animal food. Applicant has established by experiments that such animal food whether dry animal food or moist animal food described in U.S. Pat. Nos. 3,119,691 Ludington et al. and 3,202,514 Burgess et al. either have minimal palatability as dry animal food or lose palatability as in the case of moist animal food, but such palatability can be greatly enhanced by the use of greater than 0.5% by weight of yeast as a coating on such animal food.

By applying yeast as a surface coating to animal food or orally-administered medicaments in the ranges according to this invention even though a very small amount of yeast may be employed in terms of the weight percent of yeast in relation to the weight of the ingesta it is possible to obtain a substantially 100% yeast concentration on the surface of the ingesta and the yeast is able to function in the manner discovered according to the present invention, i.e., as a compound that markedly improves palatability. When the yeast is employed in admixtures with the ingesta, palatability will be reduced by virtue of the dilution effect of the ingesta on the yeast. Consequently, slightly higher concentrations of the yeast are preferred when it is combined with ingesta as an admixture.

By experimentation easily accomplished by a person with ordinary skill in the art, a minimum concentration of yeast within the aforementioned ranges can be ascertained which will improve palatability and, accordingly, the aforementioned ranges of concentrations of yeast in combination with the ingesta represent the numerical parameters for the use of yeast as a compound to improve the palatability of oral ingesta. The yeast is therefore used in combination with the ingesta in an amount sufficient to enhance the palatability and is readily distinguished from the prior art where yeast has been employed as an additive in such small amounts that no palatability improvement has been obtained because of the dilution factor which masked or hid the taste-enhancing qualities of the yeast.

Although the yeast is one embodiment is combined with the ingesta by itself the yeast may also be mixed with a binder, such as fat, e.g., tallow fat, or other edible binders known in the food art such as, starch binders, pre-cooked potato flour, pre-gelatinized starch, pre-gelatinized corn flour or the equivalent thereof, such as polymerized alkylene oxides, e.g. ethylene oxide, carrgeenins, alginates, locust bean gum, gum karaya, gum tragacanth and guar gum. Carboxymethyl cellulose may also be employed in this regard. When the yeast is employed in combination with a binder anywhere from about 5% to about 95% by weight, especially from about 20% to about 80% by weight of yeast to binder may be employed.

The yeast or yeast and binder may be combined with the ingesta by applying such yeast as a coating to animal food by first moistening the surface of the animal food to convert the farinaceous material and/or proteinaceous material at the surface into a semi-moist tacky adhesive substrate onto which the dry yeast or yeast and binder may be applied after which the food thus coated may be dried so that the overall moisture content will be within any parameters desired. The yeast and binder may also be applied to the surface of ingesta as a coating or admixed with the ingesta.

Since the yeast with or without a binder of the present invention may provide a suitable substrate for the growth of mold or bacteria especially when used in combination with moist animal food, anti-mycotic and/or anti-bacterial agents may be optionally employed in combination with the yeast or yeast and binders to inhibit such development of mold and bacteria. Standard anti-mycotic and/or anti-bacterial agents known in the art may be employed each in amounts from 0.1% to about 2.5% by weight of the yeast although amounts as low as 50 p.p.m. may be used.

By way of example, anti-mycotic agents employed in this aspect of the invention include propylene glycol, diethyl pyrocarbonate, proprionic acid, sodium and calcium proprionate, benzoic acid, sodium benzoates, sorbic acid, potassium and calcium sorbate, menadione sodium bisulfite (vitamin K). Vitamin K is especially preferred in this respect. Art-known Bacteriostatic compounds may also be employed in the yeast such as acidulants, sugars, sodium chloride, and where high moisture binders or ingesta are employed, sorbitol, propylene glycol and other art-known equivalents that provide protection due to the osmotic pressure effect of such additive. These anti-mycotic agents and/or anti-bacterial agents or any combination thereof may be incorporated into the ingesta as well in an amount from about 0.1 to about 2.5% by weight of the ingesta and in some instances in amounts as low as 50 p.p.m.

The following examples are illustrative.

EXAMPLE 1

A load of white bread based on white flour, water, milk, shortening, sugar and salt was prepared according to a standard recipe utilizing commerically-available baker's yeast as the leavening agent. The bread was cut into approximately $\frac{1}{4}''$ cube croutons and dried at 110° F. for two hours and subsequently coated in one instance with 12% by weight of primary dried yeast *Saccharomyces cerevisiae*, and in another instance, 12% by weight of primary dried torula yeast *Torulopsis utilis*, the weight percent of the coating in both instances being based on the weight of the dried croutons.

The coating in each instance was applied by placing the yeast in the bottom of a container and adding a weighed amount of the croutons thereto and rotating the container until all the croutons were coated. It was observed that the dried yeast adhered to or was in place on the surface of the croutons due to the porosity of the croutons or various interstices on the surface of the croutons into which the particles of dried yeast were adhered, trapped or held as a coating.

Upon presenting a common house cat a two ounce portion of the croutons coated with the primary dried torula yeast as described in this example the coated croutons were immediately consumed by the animal. Prior to presenting the coated croutons, the animal was regularly fed so that it was not unduly hungry when given the coated croutons, i.e., an ordinary food regimen was maintained to assure that the animal was not excessively hungry when presented with the coated croutons. The same results were obtained with the croutons coated with the primary brewer's dried yeast as described in this example, i.e., *Saccharomyces cerevisiae*.

EXAMPLE 2

The method of preparing the white bread of Example 1 was repeated employing a standard recipe, however, the white wheat flour was partially replaced with 15% by volume of commercially-available soy bean powder which had been ground to about the same consistency as the white wheat flour.

The bread obtained in this instance again was cut into approximately ¼' cube croutons dried at 110° F. for two hours and coated with the same yeasts and in the same manner described in Example 1. Two ounce portions of the yeast-coated croutons thus prepared were presented to a common house cat and each portion was immediately consumed by the animal. Again, the animal was given a regular regimen of food prior to feeding it the coated croutons to assure that it was not excessively hungry.

EXAMPLE 3

A four ounce portion of commercially-available moist dog food prepared in accord with U.S. Pat. No. 3,202,514 Burgess et al. was presented to a common house cat for four days and only about two ounces of the portion was eaten by the animal. On the fourth day, the portion that was not consumed was then moistened lightly at the surface and 12% by weight of primary dried yeast *Saccharomyces cerevisiae* based on the moistened food was applied thereto as a coating and presented to the animal whereupon it was immediately consumed.

EXAMPLE 4

A medicament was prepared for oral administration to be used in the control of round worms (*toxascaris leonina*) by admixing 0.25 oz. primary dried yeast *Saccharomyces cerevisiae* with 0.0125 oz. of piperazine adipate. The medicament thus prepared was presented to a common house cat and it was immediately consumed. Piperazine adipate was administered again to the animal in 30 days by preparing a medicament as described in this example however using 0.25 oz. primary dried torula yeast *Torulopsis utilis* and such medicament was immediately consumed.

EXAMPLE 5

A preparation was made comprising a commercially-available cereal, rolled oats, by adding 1 cup of oats to 2 cups of boiling water to which was added ⅛ teaspoon of salt. The preparation was cooled to room temperature (about 72° F.) and a 2 oz. portion presented to a common house cat; however, the animal would not eat the preparation. Two ounces of the preparation was then mixed with 0.5 oz. of dried torula yeast described in the previous example and the animal consumed the entire portion.

EXAMPLE 6

Commercially prepared dry cat food kibs were coated with 10% by weight of primary dried torula yeast, *Torulopsis utilis*, in one instance and in another instance with 10% by weight of primary dried yeast, *Saccharomyces cerevisiae*, the weight percent of the coating in both instances being based on the weight of the dry cat food kibs. The yeast employed in each instance had a moisture content of about 7% by weight.

The coating in each instance was applied by placing the yeast in the bottom of a container and adding a weighed amount of dry animal food kibs thereto and rotating the container until all dry cat food kibs were coated. It was observed that the dried yeast adhered to or was in place on the surface of the dry cat food kibs due in part to the porosity of the kibs or various interstices on the surface of the kibs into which the smaller particles of dried yeast were adhered, trapped or held. The porous nature of the surface of the dry cat food kibs traps the dry yeasts in a manner sufficient to contain the yeast as a surface coating.

A four ounce portion from a freshly opened package of the same dry cat food kibs which were not coated with dry yeast was placed in an animal feeding dish and presented to a common house cat for three days and was only partially eaten i.e. an estimated 1 oz. portion was eaten by the animal. Upon presenting the animal a 2 oz. portion of dry cat food kibs coated with primary dried torula yeast as described in this example the coated kibs were immediately consumed by the animal. Prior to presenting the coated kibs, the animal was regularly fed table scraps as a supplement to the uncoated kibs so that the animal was not unduly hungry when given the coated food kibs i.e. an ordinary food regimen was maintained to assure that the animal was not excessively hungry when presented with the coated dry cat food kibs. The same results were obtained with the kibs coated with the primary brewer's dried yeast as described in this example i.e. *Saccharomyces cerevisiae.*

EXAMPLE 7

In another experiment, approximately 3 oz. of dried cat food kibs that had been presented continuously to a common house cat for three days and which were not consumed were coated with 10% by weight of dried (8% water by weight) secondary brewer's yeast, *Saccharomyces cerevisiae,* in the manner previously described. When the coated kibs were presented to the animal they were completely consumed. Again the animal was fed with supplementary table scraps for the aforementioned three day period so that it would not be unduly hungry when presented with the yeast coated dry cat food kib.

It can be seen by employing the article of manufacture of the present invention that ingesta such as animal food can be prepared which has improved palatability and additionally the compound for enhancing the palatability of the ingesta such as an animal food is high in essential B vitamins as well as proteins. It is unexpected that a compound which is high in nutritive value also imparts improved palatability to animal ingesta. It is also unexpected that improved palatability for animal ingesta employed for the nutrition or medication of dogs or cats is obtained with a non-meat source such as the yeasts employed according to the present invention. It is even more unexpected that a non-meat compound such as the yeasts of the present invention can be combined with a non-meat ingesta and the ingesta thus obtained would be eaten by a carnivore as illustrated in the Examples. According to the prior art methods, meat, meat extracts, and the like were employed such as beef, beef broth or other beef extracts and fish scrap or fish extracts in order to improve the palatability of carnivore ingesta. It is also unexpected that a non-meat product of the present invention would improve the palatability of a meat based animal food for a carnivore as illustrated in the Examples.

Various ranges have been employed throughout the specification to describe the various parameters of the invention however it is intended that where a range of properties is given that this range is to include any range falling within the range as well as any individual value within the range. By way of example and not limitation, the yeast is described in one instance as from about 0.5% to about 99% by weight of the ingesta and a narrower range such as about 1% to about 99%, about 2% to about 99%, about 5% to about 80% by weight as well as any single value within the range such as 0.9, 3, 7.5, 12, 15% and the like are intended to be included within this range. As a further example, the moisture content of the yeast employed is given as anywhere from about 5% to about 10% by weight and again the range is intended to include a narrower range within the range such as from about 6 to about 8% and any value falling within the range such as 7%, 9% and the like. This definition of the ranges of values is also to include the ratio of yeast to binder if the binder is optionally employed, anti-mycotic and anti-bacterial agents as well as every other value given in the specification as a parameter or a set of parameters for practicing the invention set forth herein.

Although the invention has been described by reference to some preferred embodiments it is not intended that the novel article of manufacture and the method for making the same be limited thereby but that certain modifications are intended to be included within the broad scope and spirit of the preceding disclosure and the following claims.

What is claimed is:

1. As an article of manufacture, oral ingesta for animals selected from a member of the group consisting of dog food, dog medicaments, cat food and cat medicaments, said oral ingesta being combined with yeast in an amount sufficient to impart improved palatability to said oral ingesta, said yeast being selected from a member of the group consisting of the genera Saccharomycodes, Schizosaccharomyces, and Oosporidium.

2. The article of manufacture of claim 1 where said yeast comprises Saccharomycodes.

3. The article of manufacture of claim 1 where said yeast comprises Schizosaccharomyces.

4. The article of manufacture of claim 1 where said yeast comprises Oosporidium.

5. A process for improving the palatability of oral ingesta for dogs selected from a member of the group consisting of dog food and dog medicaments comprising combining said oral ingesta with yeast in an amount sufficient to impart improved palatability to said oral ingesta, said yeast being selected from a member of the group consisting of the genera Saccharomycodes, Schizosaccharomyces, and Oosporidium and feeding said oral ingesta in combination with said yeast to a dog.

6. The process of claim 5 where said yeast comprises Saccharomycodes.

7. The process of claim 5 where said yeast comprises Schizosaccharomyces.

8. The process of claim 5 where said yeast comprises Oosporidium.

9. The article of manufacture of claim 1 where said yeast is used in an amount from about 1% to about 99% by weight.

10. The article of manufacture of claim 1 where said yeast is used in an amount from about 2% to about 99% by weight.

* * * * *